United States Patent [19]

Rayhanabad

[11] Patent Number: 4,712,551
[45] Date of Patent: Dec. 15, 1987

[54] VASCULAR SHUNT

[76] Inventor: Simon B. Rayhanabad, P.O. Box 2200, Long Beach, Calif. 90801-2200

[21] Appl. No.: 918,148

[22] Filed: Oct. 14, 1986

[51] Int. Cl.⁴ .................. A61B 17/04; A61M 5/00; A61M 21/00

[52] U.S. Cl. .................. 128/334 R; 604/8; 604/101; 604/96

[58] Field of Search .............. 604/96, 8, 101; 128/334 R, 344, 325; 623/1, 12

[56] References Cited

U.S. PATENT DOCUMENTS

| | | | |
|---|---|---|---|
| 3,435,824 | 4/1969 | Gamponia | 128/334 R |
| 3,516,408 | 6/1970 | Miller, Jr. et al. | 604/96 |
| 4,119,100 | 10/1978 | Rickett | 604/96 |
| 4,377,169 | 3/1983 | Banks | 604/8 |
| 4,577,631 | 3/1986 | Kreamer | 128/334 R |

*Primary Examiner*—Richard C. Pinkham
*Assistant Examiner*—Gary Jackson
*Attorney, Agent, or Firm*—Charles H. Thomas

[57] ABSTRACT

A vascular shunt is employed for use in surgical by-pass operations to divert blood flow during an operation from the aorta into a plurality of arteries serving different organs of the body. The vascular shunt is comprised of a hollow, flexible inlet tube with an inlet tip projecting therefrom and turned to form an inlet mouth. The tip is adapted for insertion into an incision surgically formed into the wall of a human aortic artery so that the mouth of the inlet tip is directed upstream into the aorta. A releasable inlet sealing means is connected to the inlet tip to lock blood flow in the aorta downstream beyond the inlet tip. Tubular branches emanate from the inlet tube. Each branch is of a smaller internal cross-sectional area than the inlet tube and is adapted for connection to an artery serving an organ of the human body.

18 Claims, 9 Drawing Figures

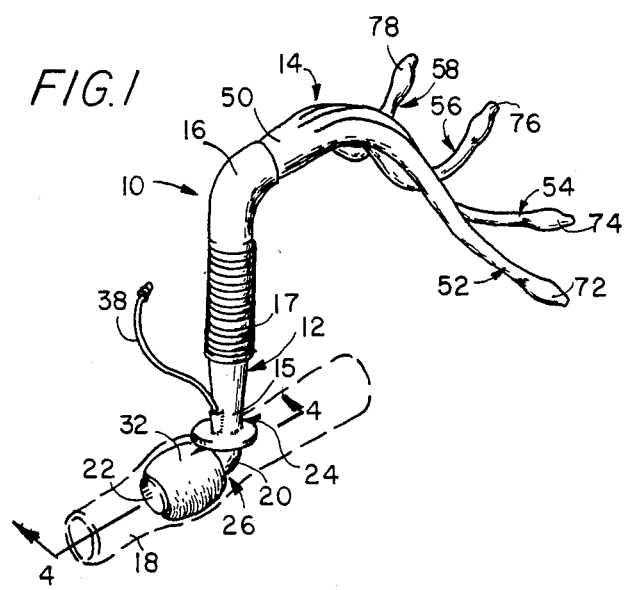
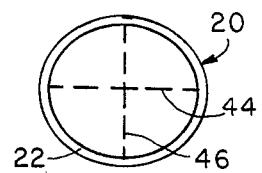
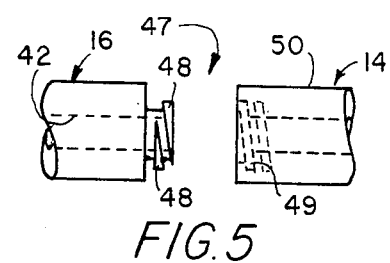
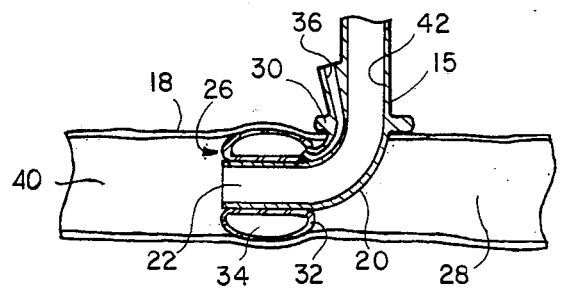
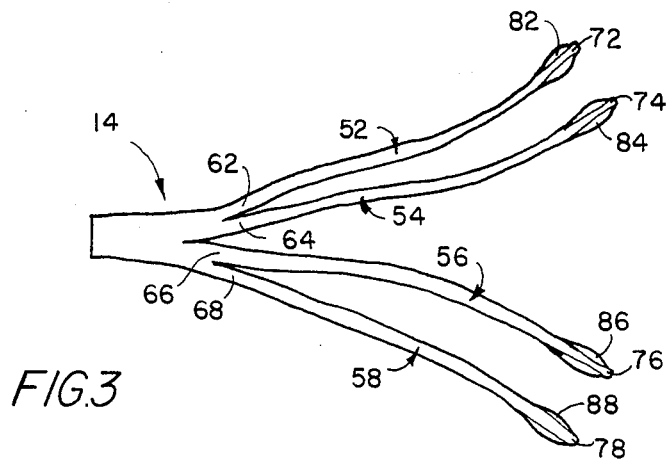

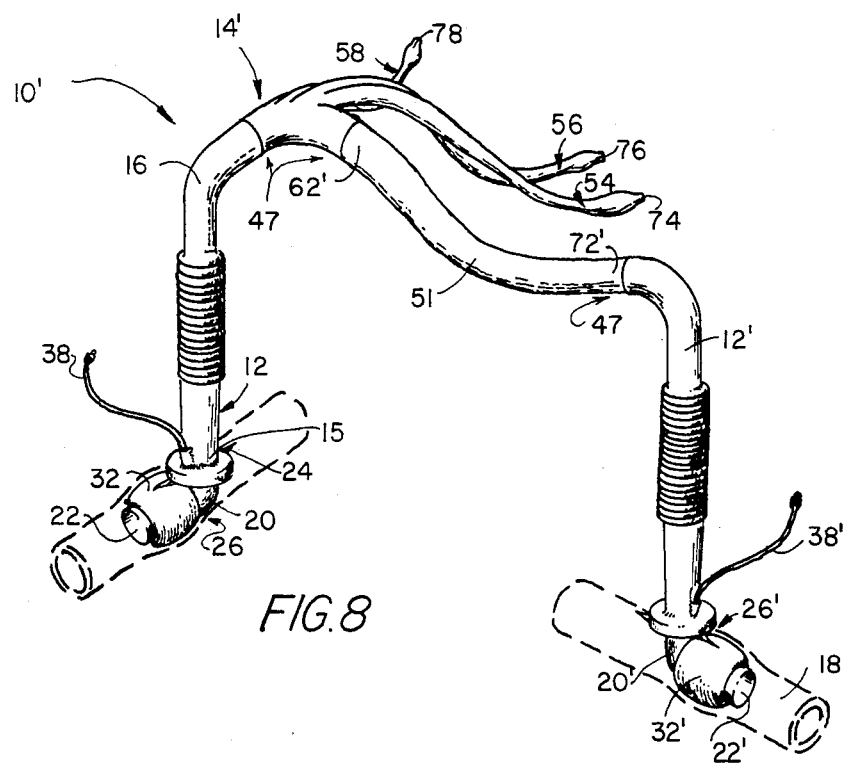
FIG.8
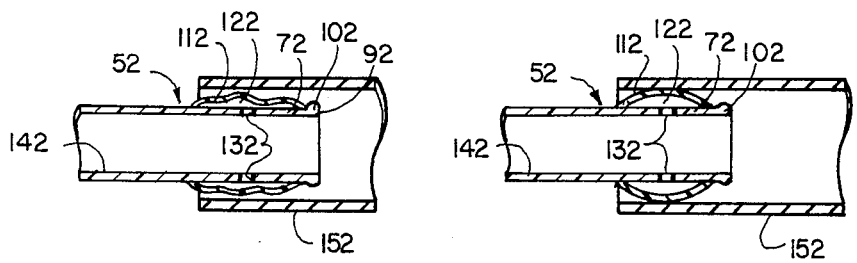
FIG.6
FIG.7
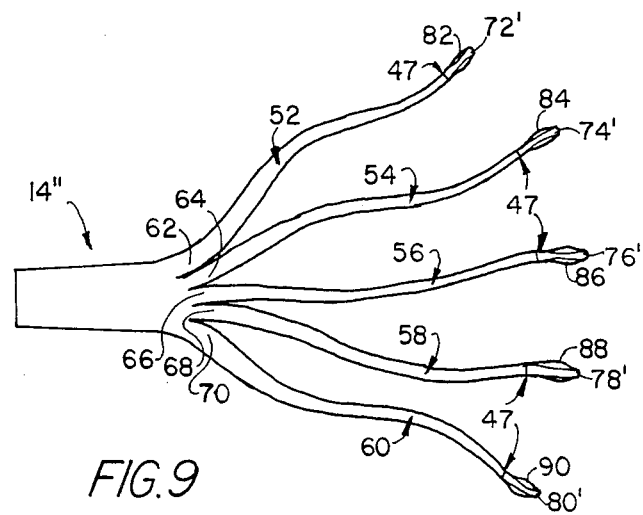
FIG.9

VASCULAR SHUNT

BACKGROUND OF THE INVENTION

1. Field of the Invention

The present invention relates to a vascular shunt for use in surgical procedures for diverting blood flow from an aorta into a plurality of different arteries, each of which carries blood to a different organ in the human body.

2. Description of the Prior Art

In the past, vascular shunts have been utilized in surgical procedures for by-passing a section of a main artery. Such vascular shunts channel blood flow from the heart into a tubular passageway past a section of an artery upon which surgery is to be performed. The blood is reintroduced into the same or a different artery at a downstream location, thereby by-passing a portion of the artery to enable that portion to be surgically repaired. For example, one such conventional shunt is sold as the Pruitt-Inahara "T" Carotid Shunt under U.S. Pat. No. 3,435,824.

Conventional shunt devices which have heretofor been available have been designed to receive blood flow at a single inlet from an arterial source and to divert that flow to a single outlet, such as the same artery at a downstream location or to blood processing equipment. During conventional surgical procedures such as operations to correct thoracal abdominal aneurysms, major organs of the body which process arterial blood, such as the bowels, kidneys, liver, spleen and spinal arteries are clamped off. However, if these organs are clamped off for an inordinately long time, they will be damaged. Indeed, a kidney is likely to be damaged if it is deprived of arterial blood for a period of about one hour. Damage to a kidney due to lack of arterial blood is oftentimes irreversible and the kidney will thereafter become useless. If this occurs, the patient has to be on dialysis for the remainder of his life. Naturally, surgical procedures which involve prolonged clamping off of the arterial blood supply to major organs are not normally undertaken, except in the most dire emergencies. However, surgical operations which involve clamping off major organs that are normally completed within a short period of time are sometimes subject to complications. Such complications lengthen the duration of the surgery, and can result in death or permanent organ damage where arteries to the kidneys and other major organs are left in a clamped condition and deprived of oxygenated blood for too long a period of time.

Hertofore, the dangers of kidney damage, and damage to other internal body organs which can result from prolonged clamping off of arterial blood supplies, have been accepted as necessary risks in surgical procedures. As a result, complications during surgery have occurred, and continue to occur, utilizing conventional surgical techniques and conventional arterial clamping devices.

SUMMARY OF THE INVENTION

The present invention is a vascular shunt used for diverting aortic blood flow in surgical by-pass procedures. The vascular shunt of the invention is comprised of a hollow, flexible inlet tube having proximal and distal extremities, with reference to the aorta. A hollow, inlet tip is located at the proximal extremity of the inlet tube and has a terminus which is oriented at an angle relative thereto. The inlet tip is adapted for insertion into an incision in the wall of an aorta of a living being. Some form of releasable sealing means is connected to the hollow inlet tip and is selectively operable to block blood from flowing in the aorta downstream past the inlet tip. Unlike prior devices, the vascular shunt of the present invention is also comprised of a plurality of branches from the distal extremity of the inlet tube, each branch having a cross-sectional area smaller than the maximum cross-sectional area of the inlet tube. Each branch has a free extremity to temporarily supply blood diverted from the aorta to a body organ.

In one preferred embodiment, the vascular shunt of the invention includes a celiac branch, a superior mesenteric branch, a right kidney branch, and a left kidney branch. In another embodiment a spinal branch is also provided. The free extemities of these branches may include collars which are expandable within arteries that lead to body organs so as to ensure that internal bleeding is controlled at the junctions between each free branch extremity and arteries joined therewith, and to ensure that blood flow is directed into arteries serving vital body organs.

To enable blood to be supplied to a body organ, the main artery leading to that organ may either be severed to allow the free extremity of a branch to be inserted coaxially into the severed end leading to the body organ, or an incision may be formed in the wall of the main artery leading to the body organ, and a free branch extremity may be inserted radially into the incision. In either event, some sort of sealing machanism, such as an expandable collar, should be employed to minimize internal bleeding so as to ensure that a sufficient amount of arterial blood reaches the intended body organs.

Where the free extremities of the branches are inserted coaxially into the severed end of an artery leading to a body organ, the sealing machanism may be provided by merely tapering the end of the free extremities so as to form a friction seal coaxially within the artery. Preferably, however, the sealing mechanism is more secure and may take the form of an inflatable collar disposed about a free branch extremity. The free distal branch extremity and the inflatable collar together form a discharge tip. Radial ports are defined in the wall of the distal branch extremity to provide communication between the central branch passageway and a chamber enclosed by a collar disposed about the wall of the distal branch extremity. That is, the collar forms an annular chamber between the inner surface of the collar and the outer surface of the tubular structure forming the free branch extremity. The ports define flow passageways, whereby a small quantity of blood under pressure may pass from the central branch passageway into the annular chamber and inflate the collar radially outwardly. Where the free branch extremity or discharge tip has been inserted coaxially into a severed artery, the blood under pressure will fill the enclosed chamber and expand the collar radially outwardly to establish a seal between the collar and the inner wall of the artery leading to the body organ, thereby limiting or preventing bleeding altogether at the junction of the discharge tip with the severed artery. Further arterial blood thereupon passes from the branch discharge tip passageway and into the artery, thereby supplying needed arterial blood to the body organ.

Such inflatable balloon-type sealing mechanisms are currently employed in other applications and are marketed commercially under the trade designation "Mayo Tips" by American Converters, a division of American Hospital Supply, Evanston, Ill. 70201.

Where the main artery to be supplied with arterial blood is of a sufficient diameter, a branch discharge tip is preferably radially inserted through an incision in the wall of the artery. This avoids totally severing of the artery and thereby accelerates healing of the artery once surgery has been completed. In such an interconnection the extremity of a branch discharge tip is turned, preferably of an angle of between 80 and 90 degrees, to form an elbow which defines a discharge mouth. Due to the elbow configuration, the discharge mouth is adapted for orientation to face in a downstream direction within the artery. In such an embodiment the sealing collar may take the form of a pneumatically inflatable collar, jacket or envelope disposed coaxially about the discharge mouth to define an inflatable chamber. This inflatable chamber may take the form of a Mayo Tip, of the type previously described, or the chamber may be pneumatically inflated by means of a narrow inflation tube which leads to the envelope and which may be inflated and deflated by pneumatic pressure applied externally of the patient.

While there are a plurality of discharge tips, one at the end of each tubular branch of the vascular shunt of the invention, the invention employs a single, flexible tubular inlet end. The inlet end is formed as a hollow tube having proximal and distal extremities, considered relative to the aorta. The proximal extremity is formed into a hollow, inlet tip turned at an angle of preferably between about 80 and about 90 degrees. The inlet tip is shaped as an elbow which forms an inlet mouth. The inlet tip is adapted for insertion into an incision surgically cut in the wall of an aorta. Once the inlet tip is readially inserted into the incision the inlet mouth is directed to face upstream in the aorta. The shape of the inlet tip is similar to that disclosed in U.S. Pat. No. 2,940,128 and employed in the Argyle THI Angled Aortic Perfusion Cannula distributed by Sherwood Medical Industries of St. Louis, Mo. 63103. A releasable sealing means is connected to the inlet tip to block blood flow in the aorta from passing beyond the inlet tip.

In a preferred embodiment of the vascular shunt of the invention,, the inlet sealing means is comprised of a pneumatically inflatable collar, envelope or jacket disposed about the mouth of the inlet tip. A pneumatic tube for inflating and deflating the collar is connected in communication with a chamber defined by the collar. The pneumatic tube extends outside of the patient and terminates externally of the tubular inlet. The collar defines an annular chamber about the projecting tip which can be expanded and contracted radially within the aorta. When the chamber is pneumatically inflated by pressure applied to the end of the tube located externally of the patient, the collar swells and presses radially outwardly against the internal wall of the aorta, thereby establishing a seal therewith. All aortic blood ariving from the left ventrical of the heart is diverted into the inlet mouth and through the vascular shunt of the invention to the arteries connected thereto leading to vital body organs. This enables surgery to be performed on the aorta downstream from the inlet tip, and ensures that the vital body organs are supplied with aortic blood even if surgery becomes protracted. Vital body organs, such as the kidneys are not subjected to a prolonged interruption of aortic blood flow, and thereby are not subjected to the likelihood of permanent, irreparable damage which would otherwise result from prolonged surgery.

The invention may be described with greater clarity and particularity by reference to the accompanying drawing figures.

DESCRIPTION OF THE DRAWINGS

FIG. 1 is a perspective view of one embodiment of the vascular shunt of the invention shown in operative position relative to an aorta.

FIG. 2 is sectional view of the inlet mouth of the vascular shunt of FIG. 1.

FIG. 3 is a plan view illustrating the discharge portion of the embodiment of the vascular shunt of FIG. 1.

FIG. 4 is a longitudinal sectional view taken along the lines 4—4 of FIG. 1.

FIG. 5 illustrates one manner of interconnection of interchangeable sections of the vascular shunt of FIG. 1.

FIG. 6 illustrates a discharge tip of the vascular shunt of the invention inserted into a severed artery prior to inflation.

FIG. 7 illustrates the discharge tip of FIG. 6 subsequent to inflation.

FIG. 8 illustrates an alternative embodiment of the vascular shunt of the invention.

FIG. 9 is a plan view of a discharge portion of another alternative embodiment of the vascular shunt of the invention.

DESCRIPTION OF THE EMBODIMENTS

FIG. 1 illustrates a vascular shunt 10 for diverting aortic blood flow in certain surgical bypass procedures, such as surgery to correct thoracal abdominal aneurysms. The vascular shunt 10 is comprised of a single, flexible tubular inlet end portion 12, having a single inlet and a branched portion 14 having a plurality of discharge outlets. The tubular inlet end 12 is constructed as a hollow, flexible inlet tube having a proximal extremity 14 and a distal extremity 16, considered relative to an aorta, for example the aorta 18 of a human patient. The inlet end 12 has an inlet tip 20 located at the proximal extremity 15 and projecting therefrom at an angle. The inlet tip 20 is best depicted in FIG. 4 and is shaped as an elbow which is turned to form a mouth 22. The tip 20 is adapted for insertion into an incision 24 surgically formed in the wall of the aorta 18. As depicted in FIG. 4, the mouth 22 of the tip 20 is directed upstream in the aorta 18.

A releasable inlet sealing means 26 is connected to the hollow, inlet tip 20 and is selectively operable to block blood flow in the aorta 18 past the inlet tip 20 and downstream therefrom in the region indicated generally at 28 in FIG. 4. The inlet tip 20 is formed at approximately an 80 degree angle relative to the inlet end 12 and has a terminus that extends upstream a distance of about or substantially equal to one inch from the center line of the proximal extremity 15 of the inlet end 12. A radial flange 30 on the proximal extremity 15 abuts against the outer wall of the aorta 18 to approximately center the inlet mouth 22 within the aorta 18 and to limit bleeding from the incision 24.

The inlet sealing means 26 is comprised of an inflatable collar, envelope or balloon 32 disposed coaxially about the mouth 22 of the inlet tip 20 and sealed by adhesive to the outer wall thereof. The collar 32 defines an annular, inflatable chamber depicted at 34. A passageway 36 is defined through the structure of the inlet tip 20 and through the proximal extremity 15 of the vascular shunt 10 to define a path of pneumatic flow into and out of the chamber 34. As depicted in FIG. 1, the releasable inlet sealing means 26 is also comprised of a pneumatic tube 38 which is inserted into the accessible opening in the passageway 36. The pneumatic tube 38 is used for inflating and deflating the collar 32 connected thereto through the passageway 36. A tube 38 extends from the proximal extremity 15 and terminates externally of the tubular inlet tip 20 and externally of the patient.

As illustrated in FIG. 4, once the inlet tip 20 has been inserted through the incision 24 and the inlet mouth 22 has been properly positioned in the aorta 18, the collar 32 may be inflated by means of the tube 38. Air is introduced into the chamber 34 through the passageway 36, thereby expanding the collar 32 radially outwardly against the interior wall of the aorta 18. Aortic blood in the upstream region 40 of the aorta 18 is blocked from flowing to the downstream region 28, and instead is diverted into the mouth 22 and through the vascular shunt passageway 42 defined through the hollow vascular shunt 10.

The inlet tip 20 is preferably formed of pliable, soft rubber. To best conform to the physical structure of the aorta 18 in different patients, the mouth 22 of the inlet tip 20 preferably defines an opening of elliptical cross section having a major axis indicated at 44 in FIG. 2 and a minor axis indicated at 46. Preferably, the dimension of the major axis 44 is about or substantially equal to 0.33 inches. Preferably also, the dimension of the minor axis 46 is about or substanially equal to 0.25 inches.

In the vascular shunt 10 the cross-sectional area of the inlet end 12 increases from the mouth 22 defined in the inlet tip 20 at the proximal extremity 15 toward the distal end 16. The inlet end 12 of the vascular shunt 10 remote from the inlet tip 20 at the distal extremity 16 defines a passageway of circular cross-section having an interior diameter of about or substantially equal to 0.75 inches.

As previously indicated, the inlet end 12 of the vascular shunt 10 is flexible, and is subject to bending. For this reason, a coil spring, visible through the transparent plastic structure of the inlet end 12 in FIG. 1, is embedded within the wall of an intermediate section 17 of the inlet end 12. The coil spring structure is provided to stiffen the walls of the inlet end 12 to prevent the walls of the passageway 42 from collapsing, even when the inlet end 12 of the vascular shunt 10 is subjected to extreme flexure. It is extremely important to prevent the passageway 42 from collapsing, since this would prevent aortic blood from reaching the downstream, branched portion 14 of the vascular shunt 10.

The vascular shunt 10 is preferably formed with a unique geometry and with dimensions especially configured to allow it to be connected between the aorta 18 and arteries for supplying aortic blood to vital organs of the human body. As previously indicated, the inlet tip 20 includes a terminal duct that extends to the mouth 22 coaxially within the aorta 18 a distance of approximately one inch. Downstream from the inlet tip 20 and from the proximal extremity 15 the inlet end 12 of the vascular shunt 10 extends a linear distance of approximately six inches. At the distal extremity 16 the inlet end 12 is permanently and inelastically deformed, as by casting to form an elbow disposed at an angle of approximately 90 degrees relative to the intermediate section 17 of the inlet end 12.

Preferably, the vascular shunt 10 is constructed of two separable sections, one of which is the inlet end portion 12 and the other which is the branched, portion 14. This construction allows different branched portions to be employed with a single inlet end 12 for different surgical procedures. Modular sections may thereby be coupled together by means of any suitable conventional coupling mechanism. The extremities of the releasably engageable portions 12 and 14 of the vascular shunt 10 are joined by a coupling 47, depicted in FIG. 5. As illustrated, the distal extremity 16 of the inlet end 12 terminates in a fitting which includes a pair of male screw threads 48 that are received in corresponding spiral female threads 49 defined in the interior wall of the upstream extremity 50 of the branched end portion 14 of the shunt 10. The plastic structure of both the inlet end portion 12 and the branched portion 14 is sufficiently resilient so that the parts of the vascular shunt 10 will remain securely coupled together when the male threads 48 are engaged with the female threads 49 and the portions 12 and 14 are twisted approximately 90 degrees relative to each other. The plastic structure of the portions 12 and 14 is stiff enough so that the coupling 47 establishes a fluid tight seal and the portions 12 and 14 will not separate under longitudinal tension exerted on the portions 12 and 14. The portions 12 and 14 may easily be separated by counter-twistin relative to each other. The coupling 47 is of the type known in the medical community as a universal attachment, such as is used to connect syringes to intravenous feeding lines.

FIG. 3 illustrates in a plan view the branched end 14 of the vascular shunt 10. The branched end 14 includes four branches, indicated at 52, 54, 56 and 58. The branch 52 has proximal and distal extremities 62 and 72, respectively, considered relative to the tubular inlet end 12. Likewise, the branch 54 has corresponding proximal and distal extremities 64 and 74. The branch 56 has proximal and distal extremities 66 and 76, respectively while the branch 58 has corresponding proximal and distal extremities 68 and 78. Each of the branches 52, 54, 56 and 58 defines a passageway of circular cross-section about or substantially equal to 0.33 inches in internal diameter at the corresponding one of the proximal extremities 62-68 thereof. The total overall length of the section of the vascular shunt 10 formed by the upstream extremity 50 of the branched portion 14 and the distal extremity 16 of the inlet end 12 lying between the proximal branch ends 62-68 and the 90 degree bend in the inlet end 12 is between about three and four inches.

Each of the branches 52, 54, 56 and 58 defines an interior passageway of a size appropriate for supplying arterial blood to a particular body organ. In the vascular shunt 10, the branched end 14 includes a celiac branch 52, a superior mesenteric branch 54, a right kidney branch 56 and a left kidney branch 58. The distal extremities 72-78 of the branches 52-58, respectively, define passageways of circular cross-section having respective interior diameters in inches of 0.250; 0.200; 0.267; and 0.167. Passageways of this size are sufficient to provide an adequate supply of arterial blood to the corresponding body organs during surgery. The branches 52 and 54 are of a size adapted for connection to arteries leading to the bowels, liver and spleen while the branches 56 and 58 are adapted for connection to arteries leading to the kidneys. All of the branches 52-58 are preferably about or substantially equal to eight to ten inches in length.

The branches 52-58 of the branched end 14 of the vascular shunt 10 are formed with radially expandable collars 82-88, as indicated. The distal extremities 72-78, with their associated expandable collars 82-88, form Mayo tips, the operation of which is best depicted in FIGS. 6 and 7. These drawing figures specifically illustrate the Mayo tip formed at the distal extremity 72 of the branch 52, although identical tips are formed at the distal extremities of each of the branches 52-58.

As illustrated in FIG. 6, the distal extremity 72 of the branch 52 terminates in a discharge mouth 92 with an outwardly protruding annular radial lip 102. Upstream from the lip 102 a collar 112 is sealed against the outer surface of the wall of the branch 56 at the distal extremity 72 to define an annular, radially expandable chamber 122 in the cavity between the interior surface of the collar 112 and the outer surface wall of the branch 56. A pair of orifices 132 are defined through the structure of the wall of the branch 52 at the distal extremity 72 to serve as radial ports allowing flow communication between the interior passageway 142 of the branch 52 and the chamber 122.

The free or distal extremity 72 and the collar 112 thereabout are of a size configuration adapted for snug insertion into the severed main celiac artery 152, as depicted in FIG. 6. The free extremity 72 of the branch 52 can easily be inserted into the severed artery 152 to the position depicted in FIG. 6, prior to the introduction of arterial blood into the passageway 142.

Once the inlet tip 20 has been installed in the aorta 18 in the manner depicted in FIGS. 1 and 4, however, and blood is introduced into the passageway 142, aortic blood will pass through the radial ports 132, thus filling the chamber 122 and expanding the collar 112 radially outwardly in the manner depicted in FIG. 7. This establishes a fluid-tight seal between the free or distal extremity 72 of the branch 52 and the exposed severed end of the celiac artery 152. Discharge sealing means are likewise established at each of the distal or free extremities 74, 76 and 78 with respect to main arteries leading to the bowels, the liver, the spleen, and the right and left kidneys.

Where an artery which is to receive arterial blood through the vascular shunt of the invention is large enough, it is preferable to connect a distal extremity of a branch of the shunt through a radial incision in the artery, thus avoiding a complete severing of the artery. Such a connection involves less surgical damage to the artery, and thereby facilitates healing.

FIG. 8 illustrates a vascular shunt 10' which is an alternative embodiment of the invention. The vascular shunt 10' is more suitable for use in surgery to by-pass the arch of the aorta to correct deterioration or aneurysms in the aortic arch, while the vascular shunt 10 is more suitable for use to correct thoracal abdominal aneurysms. The vascular shunt 10', illustrated in FIG. 8, includes many components described in connection with the vascular shunt 10. Identical components in the vascular shunt 10' are indicated with like reference numbers.

The branched end 14' of the vascular shunt 10' differs from the branched end 14 in that the branch 51' of the branched end 14' is of significantly larger diameter than the branch 52, since it must carry a large quantity of blood to be returned to the aorta 18 downstream from the inlet end 12. The interior cross-sectional area of the branch 51 is only slightly smaller than that of the inlet end 12. The branch 51 is formed by a tube which terminates at both its proximal end 62' and at its distal end 72' in a universal attachment coupling 47 of the type depicted in FIG. 5. The distal end 72' of the branch 52' leads to a discharge tube 12' which terminates in a discharge tip 20' that is turned to form an elbow. The discharge tip 20' defines a discharge mouth 22' adapted for orientation to face in a downstream direction in the aorta 18 at a location downstream from the arch of the aorta. A collar 32' is located at the discharge mouth 22' and is expandable to block blood from flowing upstream from the discharge mouth 22'. The collar 32' is inflated and deflated by the application and release of pressure externally of the patient by means of a pneumatic tube 38'. The discharge sealing mechanism 26' is of a construction identical to that of the sealing means 26, depicted in FIGS. 1 and 4, and operates in an identical manner. That is, once the discharge tip 20' has been inserted into the aorta 18 through an incision in the wall thereof, the collar 32' is pneumatically inflated through the pneumatic tube 38'. Arterial blood, arriving through the vascular shunt 10' is blocked from flowing back upstream in the aorta 18 by the expansion of the collar 32'. Consequently, arterial blood will flow only downstream in the aorta 18 thus providing sustaining and nourishing arterial blood during surgery on the arch of the aorta 18. The other three branches 54, 56 and 58 are connected to the carotid arteries to supply arterial blood to the brain during the surgery.

FIG. 9 illustrates another alternative branched end 14". The branched end 14" includes all of the branches 52-58 of the branched end 14. In addition, the branched end 14" includes a spinal branch 60 having a proximal extremity 70 and a distal extremity 80'. An expandable collar 90 is located at the distal extremity 80' and operates in the manner depicted in FIGS. 6 and 7, as priviously described. The branch 60, like the branches 52-58, is also preferably, 8-10 inches in length. The branch 60 preferably has an internal diameter of about, or substantially equal to 0.33 inches at its proximal extremity 70, and an internal diameter of about, or substantially equal to 0.125 inches at its distal extremity 80'. The distal extremity 80 is adapted for insertion into the spinal artery during surgery.

The distal extremities 72'-80' differ from the distal extremitites 72-78 in that they are interchangeably removable from the branches and may be replaced by extremities having different sizes and configurations. Such a construction allows distal extremities of an appropriate size to be selected and utilized in a modularly interchangeable manner in accordance with the size of the patient and the size of the patient's arteries. The distal extremities 72'-80' are coupled to the branches 52-60 by means of universal attachment couplings 47 of the type depicted in FIG. 5, although any suitable conventional coupling mechanism may be employed.

The several alternative branched sections 14, 14' and 14" are all of interchangeable and modular design. The may all be attached to the same inlet end 12. Each of the branched sections 14, 14' and 14" is equipped with a female coupling mechanism which forms part of a universal attachment coupling 47 of the type depicted and described in connection with FIG. 5.

The vascular shunt of the invention is a structure which provides a single inlet adapted for sealed engagement with the aorta, and a plurality of discharge outlets adapted for connection to arteries leading to the same of other arteries for supplying blood to body organs. The vascular shunt of the invention obviates the need for clamping off main arteries leading to vital organs, thus preventing damage to those organs which might otherwise be sustained as a result of deprivation of arterial blood during prolonged surgery.

Preferably, both the inlet end 12 and the branched end of the vascular shunt of the invention are formed of flexible, molded plastic, such as polyvinyl chloride. However, alternative non-toxic flexible, fluid-tight materials may also be employed.

Undoubtedly, numerous variations and modifications of the invention will undoubtedly become apparent to those familiar with vascular surgical aids. For example, a wide variety of suitable coupling mechanisms are available to join the modular shunt components together. For example, a leuer fitting or other conventional frictional or threaded fitting could be employed in place of the fitting depicted in FIG. 5. Accordingly, the scope of the invention should not be construed as limited to the particular embodiments of the vascular shunt of the invention depicted and described, but rather is defined in the claims appended hereto.

I claim:

1. A vascular shunt comprised of a single, flexible tubular inlet end, an inlet tip projecting therefrom and turned to form a mouth and adapted for insertion into an incision surgically formed into the wall of an aorta so that said mouth is directed upstream in said aorta, releasable inlet sealing means connected to said inlet tip to block blood flow in said aorta beyond said inlet tip, a plurality of tubular branches in flow communication with said tubular inlet end each terminating in a discharge tip of internal cross section reduced from the internal cross section of said inlet tip, and separate releasable discharge sealing means connected to each of said discharge tips, whereby said discharge tips are each insertable into selected arteries and said discharge sealing means limits internal bleeding at the interfaces between said discharge tips and said arteries.

2. A vascular shunt according to claim 1 wherein said inlet sealing means is comprised of a pneumatically inflatable collar disposed about said mouth of said inlet tip and a pneumatic tube for inflating and deflating said collar in communication therewith and terminating externally of said inlet tip.

3. A vascular shunt according to claim 1 wherein each of said discharge sealing means is comprised of a collar disposed about a discharge tip to define a fluid tight expandable chamber therebetween and each discharge tip has radial port means in communication with said chamber, whereby blood under pressure passes into said chamber and expands said collar radially outwardly.

4. A vascular shunt according to claim 1 wherein said mouth defines an opening of eliptical cross section having a major axis of about 0.33 inches and a minor axis of about 0.25 inches.

5. A vascular shunt according to claim 1 wherein the cross sectional area of said inlet end increases from said inlet tip and is circular with a diameter of about 0.75 inches remote therefrom.

6. A vascular shunt according to claim 5 wherein each of said branches has a proximal and a distal extremity relative to said tubular inlet end and each branch defines a passageway of circular cross section about 0.33 inches in internal diameter at said proximal extremity thereof.

7. A vascular shunt according to claim 6 wherein said branches are comprised of a celiac branch, a superior mesenteric branch, a right kidney branch, and a left kidney branch, with said distal extremities thereof defining passageways of circular cross section having respective internal diameters in inches of 0.250, 0.200, 0.167, and 0.167.

8. A vascular shunt according to claim 7 further comprising a spinal branch having a distal extremity defining a passageway of circular cross section with an internal diameter of 0.125 inches.

9. A vascular shunt according to claim 1 wherein said inlet tip includes a section of about one inch in length oriented at an angle of about 80 degrees relative to said inlet end.

10. A vascular shunt according to claim 9 including an upstream section about six inches in length from which said inlet tip projects and a downstream section between about three and four inches in length disposed relative to said upstream section at an angle of about 90 degrees relative thereto.

11. A vascular shunt according to claim 10 wherein each of said branches emanates from said downstream section and is between about eight and ten inches in length.

12. A vascular shunt for diverting aortic blood flow in surgical bypass procedures comprising a hollow, flexible inlet tube having proximal and distal extremities, a hollow, inlet tip located at said proximal extremity of said inlet tube and forming an angle relative thereto and adapted for insertion into an incision in the wall of an aorta, releasable sealing means connected to said hollow inlet tip and selectively operable to block blood from flowing in said aorta past said inlet tip, a plurality of branches in communication with said distal extremity of said inlet tube, each branch having a cross sectional area smaller than the maximum cross sectional area of said inlet tube and each having a free extremity to temporarily supply blood diverted from said aorta to a body organ.

13. A vascular shunt according to claim 12 wherein said free extremities of said branches include collars which are expandable within an artery that leads to a body organ so as to limit internal bleeding at the junction between each free branch extremity and an artery joined therewith.

14. A vascular shunt according to claim 13 wherein at least one of said free extremities forms a discharge tip that is turned to form an elbow and defines a discharge mouth adapted for orientation to empty downstream in an artery, and said collar located thereat is expandable to block blood flow upstream from said discharge mouth.

15. A vascular shunt according to claim 13 wherein said collars of at least some of said free extremities are radially expandable relative thereto, whereby said free extremities are adapted for snug insertion into a severed artery leading to a body organ and said collars are expandable to direct blood flow into each severed artery.

16. A vascular shunt according to claim 12 wherein said branches are comprised of a celiac branch, a right kidney branch and a left kidney branch.

17. A vascular shunt according to claim 16 further comprising a spinal branch.

18. A vascular shunt according to claim 12 wherein at least some of said free extremities of said branches are modular, interchangeable and detachably connected to said branches.

* * * * *